US009448421B2

United States Patent
Toner et al.

(10) Patent No.: US 9,448,421 B2
(45) Date of Patent: Sep. 20, 2016

(54) OPHTHALMIC LENS SYSTEM CAPABLE OF COMMUNICATION BETWEEN LENSES UTILIZING A SECONDARY EXTERNAL DEVICE

(71) Applicant: Johnson & Johnson Vision Care, Inc., Jacksonville, FL (US)

(72) Inventors: Adam Toner, Jacksonville, FL (US); Randall Braxton Pugh, St. Johns, FL (US); Camille A. Higham, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 14/017,790

(22) Filed: Sep. 4, 2013

(65) Prior Publication Data

US 2015/0062533 A1 Mar. 5, 2015

(51) Int. Cl.

| *A61B 3/14* | (2006.01) |
| *A61B 3/00* | (2006.01) |
| *A61B 3/10* | (2006.01) |
| *A61B 5/00* | (2006.01) |
| *G02C 7/04* | (2006.01) |
| *A61B 3/113* | (2006.01) |
| *G02C 7/08* | (2006.01) |
| *G06F 3/01* | (2006.01) |
| *H04W 4/00* | (2009.01) |

(52) U.S. Cl.
CPC ............... *G02C 7/049* (2013.01); *A61B 3/113* (2013.01); *G02C 7/04* (2013.01); *G02C 7/081* (2013.01); *G06F 3/013* (2013.01); *A61F 2250/0002* (2013.01); *H04W 4/001* (2013.01); *H04W 4/008* (2013.01)

(58) Field of Classification Search
CPC .. A61B 5/14532; A61B 3/113; A61B 3/103; A61B 3/14; A61B 3/125; A61B 3/1225; A61B 3/024; A61B 3/1015; A61B 3/107
USPC ................ 351/209, 200, 205–206, 210, 219, 351/221–222, 246–247; 600/319
See application file for complete search history.

(56) References Cited

U.S. PATENT DOCUMENTS

| 5,682,210 A | * | 10/1997 | Weirich | ......................... 348/739 |
| 5,916,179 A | * | 6/1999 | Sharrock | ........................ 600/587 |

(Continued)

FOREIGN PATENT DOCUMENTS

| CA | 2717328 A1 | 4/2014 |
| GB | 2487477 A | 7/2012 |

OTHER PUBLICATIONS

Partial European Search Report dated Jan. 19, 2015 for Application No. EP14183609.

*Primary Examiner* — Dawayne A Pinkney
(74) *Attorney, Agent, or Firm* — Carl J. Evens

(57) ABSTRACT

The present invention comprises an ophthalmic lens system capable of wireless communication through utilization of an external device, wherein the ophthalmic lens system comprises a first ophthalmic lens on a first eye and a second ophthalmic lens on a second eye, wherein the lenses may be configured to wirelessly communicate with each other by transmitting and receiving data through an external device. More particularly, in some embodiments, the external device may comprise electronic components with more computational power and energization capabilities than the ophthalmic lenses.

23 Claims, 6 Drawing Sheets

(56) References Cited

U.S. PATENT DOCUMENTS

| | | |
|---|---|---|
| 9,063,351 B1 * | 6/2015 | Ho .................... G02C 7/04 |
| 2002/0049374 A1 | 4/2002 | Abreu |
| 2003/0107707 A1 | 6/2003 | Fisher |
| 2006/0224238 A1 * | 10/2006 | Azar .................... 623/6.22 |
| 2009/0244477 A1 | 10/2009 | Pugh et al. |
| 2010/0001926 A1 | 1/2010 | Amirparviz |
| 2010/0103369 A1 | 4/2010 | Pugh et al. |
| 2010/0110372 A1 | 5/2010 | Pugh |
| 2010/0277687 A1 | 11/2010 | Shehadeh |
| 2011/0084834 A1 * | 4/2011 | Sabeta .................... 340/540 |
| 2012/0245444 A1 | 9/2012 | Otis |
| 2012/0281181 A1 | 11/2012 | Chen |
| 2013/0150004 A1 * | 6/2013 | Rosen .................... 455/414.1 |
| 2013/0170017 A1 * | 7/2013 | Caldeira et al. .......... 359/319 |
| 2013/0194540 A1 | 8/2013 | Pugh |

* cited by examiner

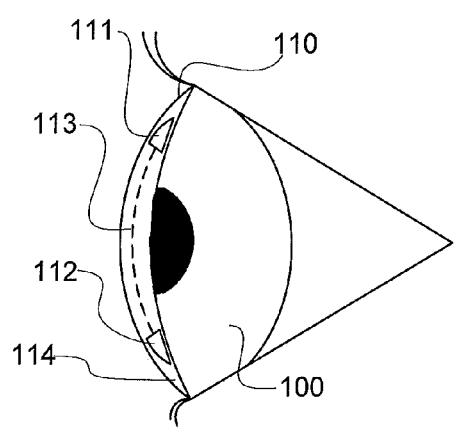
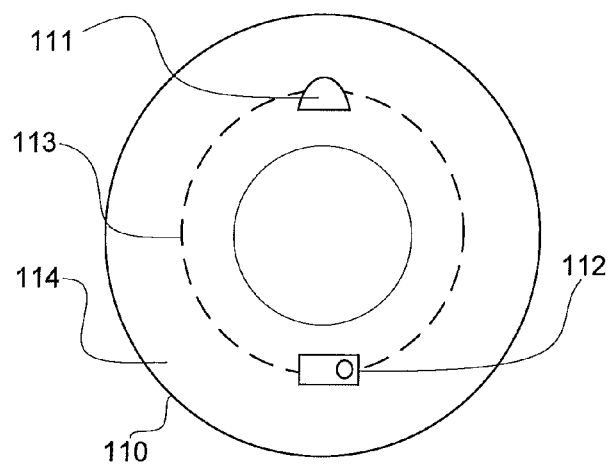
FIG. 1A
FIG. 1B
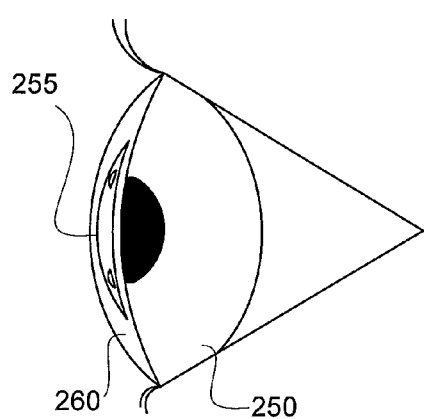
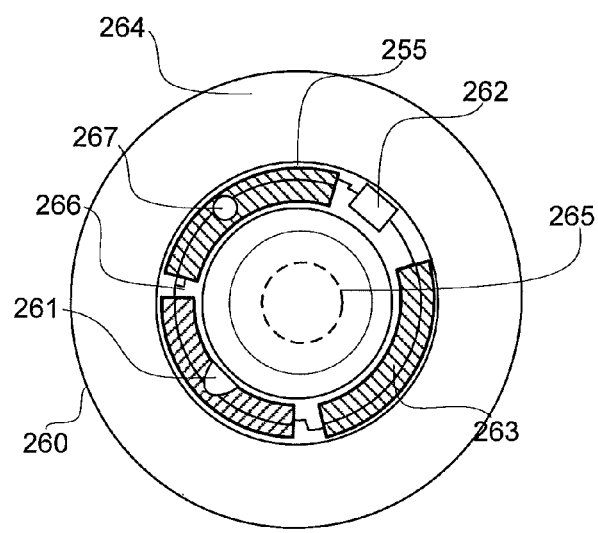
FIG. 2A
FIG. 2B

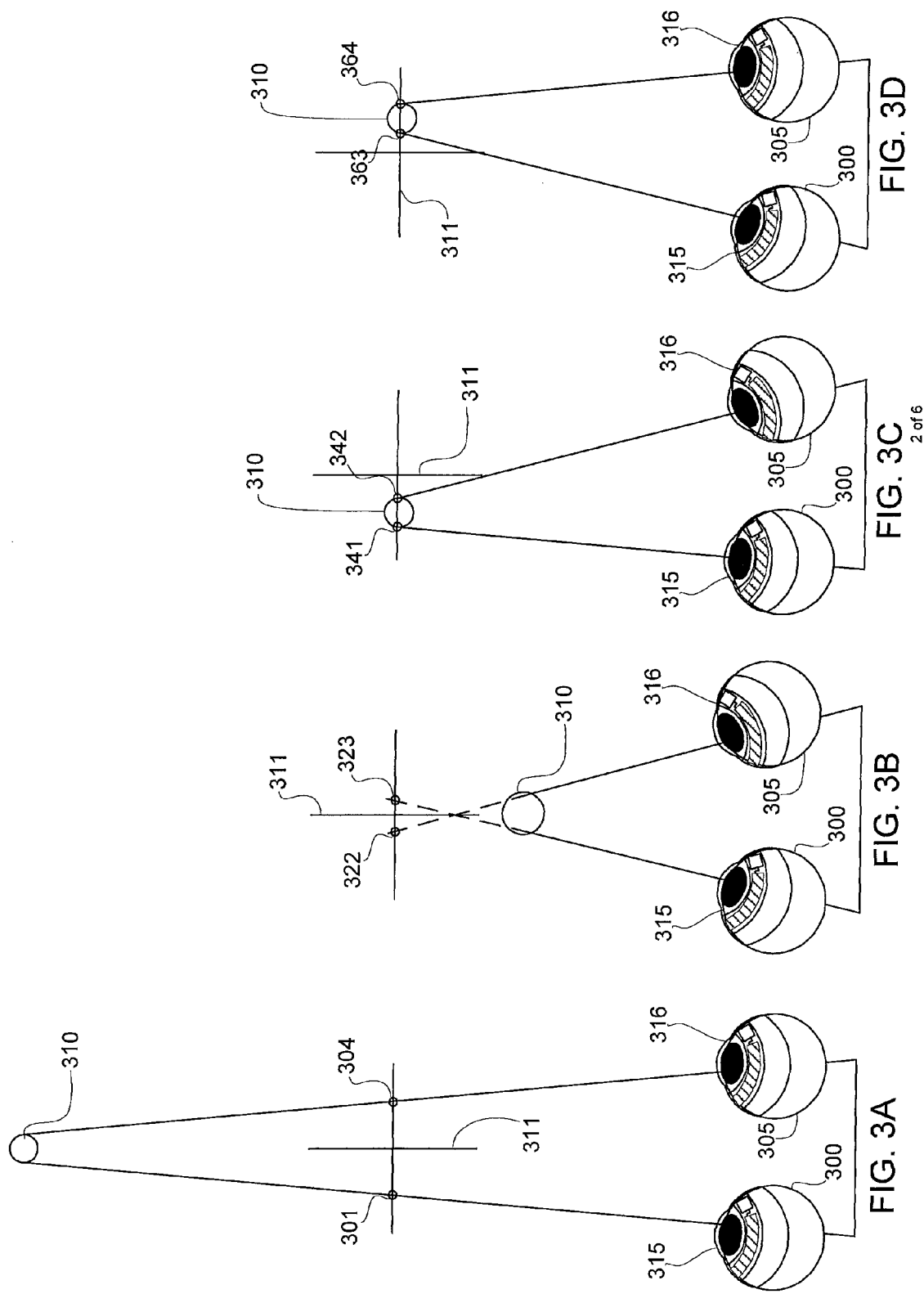

OPHTHALMIC LENS SYSTEM CAPABLE OF COMMUNICATION BETWEEN LENSES UTILIZING A SECONDARY EXTERNAL DEVICE

BACKGROUND OF THE INVENTION

1. Field of the Invention

The present invention relates to methods, apparatus, and devices associated with an ophthalmic lens system wherein the lenses may communicate with each other utilizing a secondary electronic external device. More particularly, the present invention relates to an ophthalmic lens system that may depend on the secondary electronic external device to reduce power, communication, and processing requirements within the ophthalmic lenses.

2. Discussion of the Related Art

Traditionally, an ophthalmic device, such as a contact lens, an intraocular lens, or a punctal plug included a biocompatible device with a corrective, cosmetic, or therapeutic quality. A contact lens, for example, may provide one or more of vision correcting functionality, cosmetic enhancement, and/or therapeutic effects. Each function may be provided by a physical characteristic of the lens. A design incorporating a refractive quality into a lens may provide a vision corrective function. Pigmentation incorporated into the lens may provide a cosmetic enhancement. An active agent incorporated into a lens may provide a therapeutic functionality. Such physical characteristics may be accomplished without the lens entering into an energized state.

More recently, active components have been included in a contact lens, and the inclusion may involve the incorporation of energizing elements within the ophthalmic device. The relatively complicated components to accomplish this effect may derive improved characteristics by including them in insert devices which are then included with standard or similar materials useful in the fabrication of state of the art ophthalmic lenses.

The ability for a user's ophthalmic lenses to communicate with each other may expand the possible functionalities of an energizable ophthalmic lens system. Wireless communication may allow one lens to recognize the relative position of the opposite lens, which may provide a more accurate determination of where the user may be looking. Wireless communication may also allow the two lenses to interact with each other, for example, to trigger specific, different actions when a user blinks or winks.

Communication between two contact lenses on a user may be difficult for several reasons. Each contact lens has limited area and volume for batteries and electronic components. For example, the volume available for batteries and electronic circuits in a contact lens may be less than 20 mm$^3$, whereas the volume available for all components in a smartphone may be 50,000 mm$^3$. Likewise, contact lens batteries may have 100 µA-Hr of capacity whereas a smartphone may have a capacity of 1400 mA-Hr. Thus, each contact lens may be limited in transmitter output power and receiver sensitivity.

Lower distance may be typically associated with reduced transmitter and receiver power requirements. Although the contact lenses may only be about 70 mm apart when on a user's eyes, there may not be a direct line of sight between the lenses, so direct light-based communication may not be possible without relying on reflections from nearby objects.

Further, in the event a radio frequency (RF) system may be used, the antenna area available in a contact lens, along with the dielectric properties of the eye and body, may make communication inefficient. Complex processing of signals, decision inputs, and data may also be difficult in contact lenses. The aforementioned limits on area, volume, and battery capacity may constrain the size, speed, computational complexity, and current consumption of a processor. For example, while it may be preferred for application enablement to include a powerful microcontroller or central processing unit (CPU) in contact lenses, state-of-the-art technology may not allow such integration.

Some exemplary systems may detect convergence of gaze to trigger a focus change, and without an external electronic device, the two contact lenses must obtain and transmit gaze direction, determine convergence, and signal the need to change focus. This may require communication between the lenses to carry gaze direction and focus change information. Further, this system may require tight timing synchronization between the lenses. In a system tracking gaze direction instead of just convergence, the transmission and computation requirements may be even higher.

The addition of a larger, external electronic device may permit portions of the communication and/or processing burden to be placed in the external electronic device, thereby easing the requirements on the contact lenses. Similar techniques are used in cellular communications, where a user's handset has limited battery power and limited size, and thus limited transmitter and receiver power and antenna gain. In such an example, the much larger available size and current in the cellular base station permits higher gain, power, and computational complexity.

It may be anticipated that some of the solutions for increasing wireless communication between energizable ophthalmic lenses may provide novel aspects for non-energized devices and other biomedical devices. Accordingly, there may be a need in the art for improved wireless communication between lenses, and utilizing a secondary external device may offer a solution to many of the current issues with inter-lens communication.

SUMMARY OF THE INVENTION

The addition of an external electronic device, such as a smartphone, watch, or tablet, may ease the communication requirements for an ophthalmic lens system. As described below, such a device may have much higher battery power and communication capability. Thus, it may be easier for each contact lens to communicate with a common, external device than with each other. Because of the greater area, volume, and battery capacity available in an external electronic device, the electrical requirements of the contact lens may be eased.

For example, a high-sensitivity receiver may be employed in an electronic device thereby reducing the output power requirements in a contact lens transmitter. Such a high-sensitivity receiver in the electronic device may include a low-noise amplifier (LNA), intermediate gain stages, high-dynamic-range and high-resolution analog-to-digital converter, and complex digital signal processing. In some exemplary embodiments, rather than integrating complex signal processing and microcontroller functionality into contact lenses, these functions may be performed in the external electronic device.

Such applications may even be performed in existing components of the electronic device, for example, the applications processor or CPU of the electronic device. The external device may comprise more complex and sensitive transceiver circuitry, for example, transmitter and receiver gain and signal processing.

In some applications, the functionality of the contact lenses may depend on communication with each other with or without an external device, for example, where the contact lenses comprise a variable optic portion, which may allow for adjustable powers. Other exemplary embodiments may specifically involve an electronic device, for example, one where the contact lenses may be used to control the external device. In such examples, the external device may be used to ease the requirements on the contact lenses. Accordingly, there may be a need in the art for improved wireless communication between lenses, and utilizing a secondary external device may offer a solution to many of the current issues with inter-lens communication.

Accordingly, the present invention comprises an ophthalmic lens system capable of wireless communication through the utilization of an external device, wherein the ophthalmic lens system comprises a first ophthalmic lens on a first eye and a second ophthalmic lens on a second eye, wherein the lenses may be configured to wirelessly communicate with each other by transmitting and receiving data through an external device. More particularly, in some exemplary embodiments, the external device may comprise electronic components with more computational power and energization capabilities than the ophthalmic lenses.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 1A illustrates a cross sectional view of an exemplary embodiment of an energizable ophthalmic lens on an eye, wherein the energizable ophthalmic lens may be capable of wirelessly interfacing with an external device.

FIG. 1B illustrates a front view of an exemplary embodiment of an energizable ophthalmic lens capable of wirelessly interfacing with an external device.

FIG. 2A illustrates a cross sectional view of an alternate exemplary embodiment of an energizable ophthalmic lens on an eye, wherein the energizable ophthalmic lens may be capable of wirelessly interfacing with an external device.

FIG. 2B illustrates a front view of an alternate exemplary embodiment of an energizable ophthalmic lens capable of wirelessly interfacing with an external device.

FIGS. 3A-3D illustrate a top down view of various gaze directions and convergence distances of a pair of eyes each wearing energizable ophthalmic lenses with position recognizing mechanisms.

DETAILED DESCRIPTION OF THE INVENTION

Figure 4:
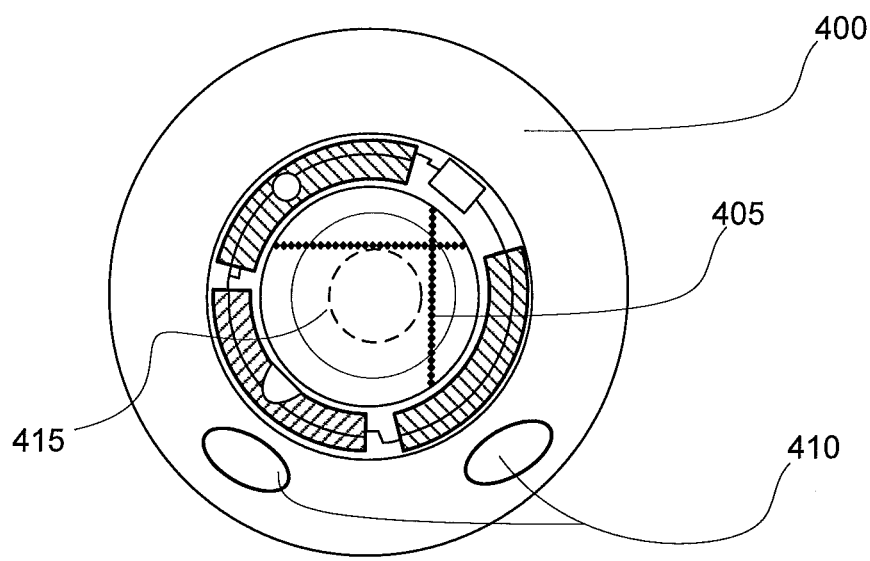
FIG. 4 illustrates an exemplary embodiment of an energizable ophthalmic lens with a position recognizing mechanism.

The present invention describes an ophthalmic lens system capable of wireless communication between ophthalmic lenses, wherein the wireless communication capabilities may be improved through use of an external device, which may offer larger volume capacity to house electronic components. In general, according to some exemplary embodiments of the present invention, the external device may be able to bear the majority of the processing and power burdens that may be associated with complex wireless communication. In addition, utilizing an external device may broaden the possible wireless communication methods, since an external device may allow for line-of-sight transmissions.

In the following sections, detailed descriptions of exemplary embodiments of the present invention will be given. The description of both preferred and alternative embodiments are exemplary embodiments only, and it is understood that to those skilled in the art that variations, modifications, and alterations may be apparent. It is therefore to be understood that the exemplary embodiments do not limit the scope of the underlying invention.

GLOSSARY

In this description and claims directed to the present invention, various terms may be used for which the following definitions will apply:

Component: as used herein refers to a device capable of drawing electrical current from an energy source to perform one or more of a change of logical state or physical state.

Electrical communication: as used herein refers to being influenced by an electrical field. In the case of conductive materials, the influence may result from or in the flow of electrical current. In other materials, it may be an electrical potential field that causes an influence, such as the tendency to orient permanent and induced molecular dipoles along field lines as an example.

Encapsulate: as used herein refers to creating a barrier to separate an entity, for example, a media insert, from an environment adjacent to the entity.

Encapsulant: as used herein refers to a layer formed surrounding an entity, for example, a media insert, that creates a barrier to separate the entity from an environment adjacent to the entity. For example, encapsulants may comprise silicone hydrogels, such as Etafilcon, Galyfilcon, Narafilcon, and Senofilcon, or other hydrogel contact lens material. In some exemplary embodiments, an encapsulant may be semipermeable to contain specified substances within the entity and preventing specified substances, for example, water, from entering the entity.

Energized: as used herein refers to the state of being able to supply electrical current to or to have electrical energy stored within.

Energy: as used herein refers to the capacity of a physical system to do work. Many uses within the present invention may relate to the capacity of being able to perform electrical actions in doing work.

Energy Source: as used herein refers to any device or layer that may be capable of supplying energy or placing a logical or electrical device in an energized state.

Event: as used herein refers to a defined set of parameters, for example, a biomarker level, energization level, pH level, or a visual recognition of a particular object. An event may be specific to a wearer, such as a level of medication, or may be generally applicable to all wearers, such as temperature.

Functionality: as used herein refers to a fundamental use or purpose of the ophthalmic lens, in contrast to auxiliary or incidental functions. Functionality may comprise, for example, vision correction, active-agent dispensing, cosmetic, external device interfacing, or three-dimensional perception of stereoscopic media. In contrast, incidental functions may comprise actions necessary to allow for operation of the fundamental purpose.

Functionalized: as used herein refers to making a layer or device able to perform a function including, for example, energization, activation, or control.

Intraocular lens: as used herein refers to an ophthalmic lens that may be embedded within the eye.

Ophthalmic lens or ophthalmic device or lens: as used herein refers to any device that resides in or on the eye. The device may provide optical correction, may be cosmetic, or provide some functionality unrelated to optic quality. For example, the term lens may refer to a contact lens, intraocular lens, overlay lens, ocular insert, optical insert, or other similar device through which vision may be corrected or modified, or through which eye physiology may be cosmetically enhanced (e.g. iris color) without impeding vision. Alternatively, lens may refer to a device that may be placed on the eye with a function other than vision correction, for example, monitoring of a constituent of tear fluid or means of administering an active agent. In some exemplary embodiments, the preferred lenses of the present invention may be soft contact lenses that are made from silicone elastomers or hydrogels, which may include, for example, silicone hydrogels and fluorohydrogels.

Lens-forming mixture or reactive mixture or RMM: as used herein refer to a monomeric composition and/or prepolymer material that may be cured and cross-linked or cross-linked to form an ophthalmic lens. Various embodiments may include lens-forming mixtures with one or more additives such as UV blockers, tints, diluents, photoinitiators, or catalysts, and other additives that may be useful in an ophthalmic lenses such as, contact or intraocular lenses.

Liquid crystal: as used herein refers to a state of matter having properties between a conventional liquid and a solid crystal. A liquid crystal may not be characterized as a solid but its molecules exhibit some degree of alignment. As used herein, a liquid crystal may be not limited to a particular phase or structure, but a liquid crystal may have a specific resting orientation. The orientation and phases of a liquid crystal may be manipulated by external forces, for example, temperature, magnetism, or electricity, depending on the class of liquid crystal.

Media insert: as used herein refers to an encapsulated insert that will be included in an energized ophthalmic device. The energization elements and circuitry may be embedded in the media insert. The media insert defines the primary purpose of the energized ophthalmic device. For example, in embodiments where the energized ophthalmic device allows the user to adjust the optic power, the media insert may include energization elements that control a liquid meniscus portion in the optic zone. Alternatively, a media insert may be annular so that the optic zone may be void of material. In such embodiments, the energized function of the lens may not be optic quality but may be, for example, monitoring glucose or administering medicine.

Optic zone: as used herein refers to an area of an ophthalmic lens through which a user of the ophthalmic lens sees.

Power: as used herein refers to work done or energy transferred per unit of time.

Rechargeable or re-energizable: as used herein refers to a capability of being restored to a state with higher capacity to do work. Many uses within the present invention may relate to the capability of being restored with the ability to flow electrical current at a certain rate for certain, reestablished time periods.

Reenergize or recharge: as used herein refers to restoring to a state with higher capacity to do work. Many uses within the present invention may relate to restoring a device to the capability to flow electrical current at a certain rate for certain, reestablished time periods.

Stabilizing feature: as used herein refers to a physical characteristic that stabilizes an ophthalmic device to a specific orientation on the eye, when the ophthalmic device may be placed on the eye. In some embodiments, the stabilizing feature may add sufficient mass to ballast the ophthalmic device. In some embodiments, the stabilizing feature may alter the front curve surface, wherein the eyelid may catch the stabilizing feature and the user may reorient the lens by blinking. Such exemplary embodiments may be enhanced by including stabilizing features that may add mass. In some exemplary embodiments, stabilizing features may be a separate material from the encapsulating biocompatible material, may be an insert formed separately from the molding process, or may be included in a rigid insert or a media insert.

Substrate insert: as used herein refers to a formable or rigid substrate that may be capable of supporting an energy source and may be placed on or within an ophthalmic lens. In some exemplary embodiments, the substrate insert also supports one or more components.

Three-dimensional perception or three-dimensional viewing: as used herein refers to where an ophthalmic device translates a two-dimensional image so that the brain interprets three-dimensional properties within the image.

Three-dimensional surface or three-dimensional substrate: as used herein refers to any surface or substrate that has been three-dimensionally formed where the topography may be designed for a specific purpose, in contrast to a planar surface.

Variable optic: as used herein refers to the capacity to change an optical quality, for example, the optical power of a lens or the polarizing angle.

Ophthalmic Lens

In some exemplary embodiments, the functionality of the energizable ophthalmic lenses may require communication between the lenses. For example, the ophthalmic lenses may allow the user to perceive stereoscopic media as three-dimensional, which may allow a user to watch "3-D" films, video games, and shows without requiring "3-D glasses", as may be typically required with such media. As non-limiting examples, the external device showing the 3-D media may comprise a television, handheld gaming device, or tablet. Some exemplary embodiments may require the lenses to alternately block the user's vision at a speed comparable to the refresh rate of stereoscopic media, which may require complex processing and power. The device may be capable of detecting the refresh rate of the stereoscopic media and may prompt the alternating vision blocking in the ophthalmic lenses.

Energizable ophthalmic lenses may assist in vision therapy, wherein a user may perform specific eye exercises.

The exercises may increase the ability of the user's brain to accommodate for damage or miscues. In some exemplary embodiments, the calibration may establish a set of goal parameters. For example, the ophthalmic lenses may be able to determine when or whether the eye movements are falling outside the acceptable range, wherein a therapy schedule may establish the acceptable range.

Such exemplary embodiments that utilize an external device to track gaze and/or convergence may reduce the power and processing burden on the ophthalmic lenses, requiring only the ability to wirelessly exchange small amounts of data and, in some instances, energize a mechanism that may control functionality within the lens. The external device may serve as the primary processing and power source for the interfacing mechanisms, which may reduce the burden on the ophthalmic lenses, which are inherently limited in size. Utilizing an external device may allow for communication requiring line of sight, which may not be practical where the bridge of the nose impedes communication between a left and right ophthalmic lens.

Referring to FIGS. 1A and 2A, exemplary embodiments of an energizable ophthalmic lens 110, 260 with interface capabilities with an external device are illustrated on an eye 100, 250. FIGS. 1B and 2B illustrate a front view of the ophthalmic lenses 110, 260. As shown in FIGS. 1A and 1B, an ophthalmic lens 110 may comprise a soft biocompatible portion 114, a processor with a receiver and/or transmitter 112, and conductive traces 113.

Some aspects may comprise additional electronic components 111 that may add to the functionality of the ophthalmic lens 110. For example, the electronic component 111 may comprise a notification mechanism, wherein a prompt from the external device may activate the event notification mechanism, such as through use of a light emitting diode, vibration, or sound device. The notification mechanism may be activated when an event, such as a phone call or incoming email, may occur on the external device; when an event, such as an energization, may occur on the ophthalmic lens; or when an event, such as a successful pairing, may occur between the ophthalmic lens 110 and the external device. For exemplary purposes, the electronic component 111 may be described as an event notification mechanism, but other functionalities may be practical and desirable. Accordingly, such variations are well within the scope of the inventive art described herein.

In some exemplary embodiments, the ophthalmic lens 110 may not comprise a power source, and the ophthalmic lens 110 may be powered through a wireless energy transmission. For example, placing the ophthalmic lens 110 in a specified proximity to an external device may charge the sensor and the notification mechanism 111. Alternatively, when an engagement prompt from either the external device or the ophthalmic lens 110 may initiate interfacing between the devices, the external device may wirelessly power the notification mechanism 111.

The components 111-113 may not be encapsulated in a media insert, and the soft biocompatible portion 114 may be in direct contact with the components 111-113. In such exemplary embodiments, the soft biocompatible portion 114 may encapsulate the components 111-113. The encapsulation may suspend the components 111-113 at a specific depth within the ophthalmic lens 110. Alternatively, the components 111-113 may be included on a substrate insert. The substrate insert may be formed and the components 111-113 may be placed on the substrate prior to the addition of the soft biocompatible portion 114.

An alternative exemplary embodiment of a media insert 255 for an energized ophthalmic device 260 on an eye 250 is illustrated in FIG. 2A, and a corresponding energized ophthalmic device 260 is illustrated in FIG. 2B. The media insert 255 may comprise an optic zone 265 that may or may not provide a second functionality, including, for example, vision correction. Where the energized function of the ophthalmic device may be unrelated to vision, the optic zone 265 of the media insert 255 may be void of material.

In some exemplary embodiments, the media insert 255 may include a portion not in the optic zone 265 comprising a substrate incorporated with energizing elements, such as a power source 263, and electronic components, such as a processor 262. In some exemplary embodiments, the power source 263, including, for example, a battery, and the processor 262, including, for example, a semiconductor die, may be attached to the substrate. In some such aspects, conductive traces 266 may electrically interconnect the electronic components 262, 261 and the energization elements or power source 263.

In some exemplary embodiments, the media insert 255 may further comprise a receiver 267, which may wirelessly detect, transmit, and receive interface data to and from an external device. The receiver 267 may be in electrical communication, such as through the conductive traces 266, with the processor 262 and the power source 263.

In some exemplary embodiments, the processor 262 may be programmed to establish the parameters of the functionality of the ophthalmic lens 260. For example, where the ophthalmic lens 260 comprises a variable optic portion in the optic zone 265, the processor may be programmed to set the energized optical power. Such an exemplary embodiment may allow for mass production of media inserts that have the same composition but include uniquely programmed processors.

The processor 262 may be programmed before the encapsulation of the electrical components 261-263, 266, 267 within the media insert 255. Alternatively, the processor 262 may be programmed wirelessly after encapsulation. Wireless programming may allow for customization after the manufacturing process, for example, through a programming apparatus in a doctor's office, a store, or a home. In some exemplary embodiments, the external device may be capable of programming an ophthalmic lens 260.

For illustrative purposes, the media insert 255 may be shown in an annular embodiment, which may not include a portion in the optic zone 265, although several possibilities may exist for the mechanical implementation of a functional insert. However, where a functionality of the media insert 255 may be related to vision, the media insert 255 may include an energizable element within the optic zone 265. For example, the media insert 255 may comprise a variable optic portion, wherein the media insert 255 may provide multiple powers of vision correction based on different energization levels. In some exemplary embodiments, the external device may comprise a control mechanism for the variable optic portion, or other adjustable functionalities. For example, the variable optic portion may be adjusted based on the viewing distance, such as for users with presbyopia. In such exemplary embodiments, as described below in relation to FIGS. 3A-3D, wireless communication between the right and left ophthalmic lens may allow the ophthalmic lens system to detect convergence The media insert 255 may be fully encapsulated to protect and contain the energization elements 263, traces 266, and electronic components 261, 262, 267. In some exemplary embodiments, the encapsulating material may be semipermeable, for example, to prevent specific substances, such as water, from entering the media insert 255 and to allow specific substances, such as ambient gasses or the byproducts of reactions within energization elements, to penetrate or escape from the media insert 255.

In some exemplary embodiments, the media insert 255 may be included in an ophthalmic device 260, which may comprise a polymeric biocompatible material. The ophthalmic device 260 may include a rigid center, soft skirt design wherein a central rigid optical element comprises the media insert 255. In some specific embodiments, the media insert 255 may be in direct contact with the atmosphere and the corneal surface on respective anterior and posterior surfaces, or alternatively, the media insert 255 may be encapsulated in the ophthalmic device 260. The periphery 264 of the ophthalmic device 260 may be a soft skirt material, including, for example, a polymerized reactive monomer mixture, such as a hydrogel material.

Referring now to FIGS. 3A-3D, a pair of eyes is illustrated gazing at an object 310 in different directions and at different distances, wherein an axis 311 is provided to establish a reference point. For illustrative purposes, a point beyond the positive y-axis of the axis 311 may be considered further than a point within the axis 311, and a point before the negative y-axis may be considered nearer than a point within the axis 311.

As shown in FIG. 3A, when an object 310 may be viewed at a far distance, both eyes may be gazing in a similar or same direction, with little convergence. For example, when looking at the object 310 from a distance, the gaze of the right eye 305 may cross the axis 311 at point 304, and the gaze of the left eye 300 may cross the axis 311 at point 301. As shown in FIG. 3B, when the object 310 may be viewed at a close distance, the eyes may converge, though still gazing forward. For example, when extended beyond the object to the axis 311, the gaze of the right eye 305 may cross the axis 311 at point 322, and the gaze of the left eye 300 may cross the axis 311 at point 323.

As shown in FIG. 3C, when the object 310 may be located left of center, the left eye may be looking forward, and the right eye may shift to look left. For example, the gaze of the left eye 300 may cross the axis 311 at point 341, and the gaze of the right eye 305 may cross the axis 311 at point 342. As shown in FIG. 3D, the opposite of FIG. 3C may occur when the object 310 may be located right of center. For example, the gaze of the left eye 300 may cross the axis 311 at point 363, and the gaze of the right eye 305 may cross the axis 311 at point 364.

In some aspects, such as illustrated, the gaze of the right eye 305 may cross the axis 311 at the same point 322 when looking at a near object 310 (FIG. 3B) and when looking at an object 310 to the left of center (FIG. 3C). Similarly, such as illustrated, the gaze of the left eye 300 may cross the axis 311 at the same point 301 when looking at a distant object 310 (FIG. 3A) and when looking at an object 310 to the left of center (FIG. 3C). Where the right ophthalmic lens 316 may not communicate with the left ophthalmic lens 315, the lenses and the external device may not be able to discern between changes in gaze prompted by a change in distance, such as illustrated between FIG. 3A and FIG. 3B, and a change in direction, such as illustrated between FIG. 3C and FIG. 3D.

Figure 5:
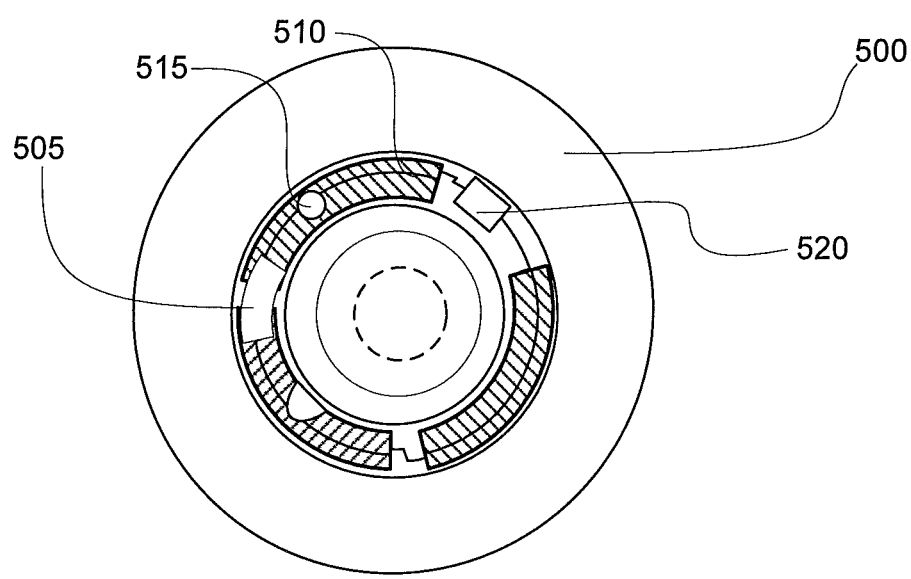
FIG. 5 illustrates an alternate exemplary embodiment of an energizable ophthalmic lens with a position recognizing mechanism

Referring now to FIGS. 4 and 5, energizable ophthalmic lenses 400, 500 with position recognizing mechanisms 405, 505 are illustrated. Pupil position and convergence detection systems 405, 505 incorporated within ophthalmic lenses 400, 500, which are positioned on eyes, may track the position of the pupils, the ophthalmic lenses 400, 500, or both. For example, the detection system may comprise reverse-facing photodetectors capable or observing pupils or accelerometers capable of tracking the movement of the eyes.

As illustrated in FIG. 4, the position recognizing mechanism 405 may detect eye movement behind the ophthalmic lens 400 and/or may detect lid position in front of the ophthalmic lens 400. In some exemplary embodiments, the ophthalmic lens 400 may comprise a sensor array 405. Where the ophthalmic lens 400 may detect lid position, the sensor array 405 may comprise one or more photosensors. Such photosensors may be placed in suitable locations on the ophthalmic lens 400 to provide enough sample locations to reliably determine lid position without obstructing the clear optic zone. For example, as illustrated, a perpendicular line of sensors may be arranged outside of the optic zone 415.

When an eyelid may be in an open position, all or most of the photosensors 405 may be exposed to receive ambient light, which may create a photocurrent detectable by an electronic circuit included in the ophthalmic lens 400. A change in lid position may limit ambient light exposure for some or all of the photosensors. The ophthalmic lens may be able to detect lid position based on varying levels of photocurrent.

A lid detection device may allow the ophthalmic lens and/or external device to recognize eye gestures, which may comprise deliberate blink or wink patterns. In some preferable embodiments, lid detection may be combined with convergence detection. Such combinations may allow the ophthalmic lens to discern deliberate lid position from unintentional lid position change, which may be caused, for example, by changing focus between objects of varying distances.

In some exemplary embodiments, a photodetector array 405 may be rear facing, allowing the ophthalmic lens 400 to track gaze. The light to the photodetector array 405 may be blocked when located outside of the pupil. When the eye may change gaze, a portion of the photodetectors 405 may be exposed to light reflected through the pupil. Accordingly, the ophthalmic lens 400 may comprise stabilizing features 410, which may allow the eye to move behind the ballasted ophthalmic lens 400.

As illustrated in FIG. 5, the pupil position and convergence detector systems may comprise several components, which may form a more complex system, including, for example, a three-axis accelerometer 505, a power supply 510, a transceiver 515, and a controller 520 comprising signal-conditioning circuitry and memory. A communication channel between the two ophthalmic lenses may allow the pupil position and convergence detection systems to synchronize on pupil position.

In some exemplary embodiments, the ophthalmic lens 500 may move with the eye. In such embodiments, the ophthalmic lens 500 may comprise one or more position recognizing mechanisms such as accelerometers 505. In some such embodiments, the accelerometers 505 may comprise piezoelectric, piezoresistive, or capacitive components, comprising, for example, piezoceramic or crystal. The accelerometers 505 may comprise a micro electro-mechanical system (MEMS). In others, such as illustrated in FIG. 4, the ophthalmic lens 400 may be ballasted by stabilization features 410, wherein the eye may move behind the lens 400.

The ophthalmic lenses may be calibrated through the external device, wherein the calibration may establish the user's preferences and attributes. The calibration may enable the lenses to track the user's eye movement more accurately. The calibration process may provide baseline data to the external device, the ophthalmic lens, or both. In some aspects, the calibration may program the ophthalmic lenses to recognize how the lenses move relative to eye movements.

Calibration may allow the external device to discern between deliberate and involuntary eye movement, for example, movement caused by nystagmus. A calibration step may prompt the user to look at an object on the screen of the external device for a predefined length of time. Throughout that time, the external device may record or recognize involuntary movement data, including the speed, direction, and distances from the initial focus point.

Based on the calibration, the external device may be able to recognize and ignore involuntary movement data, treating the data similarly to noise, as may be common in electronic devices. For users with severe or problematic nystagmus, calibration may not be sufficient to distinguish voluntary and involuntary eye movements. In some such embodiments, specialized ophthalmic lenses, additional software in the external device, or a combination of both may be necessary to adequately overcome the "noise" of involuntary eye movement. The external device may save the calibration results and process the position data from one lens based on that calibration. Accordingly, the position data transmitted to the opposite eye may already be adjusted, alleviating some of the processing burdens on the ophthalmic lenses.

The calibration may limit the chance of wearing lenses on the incorrect eye. For example, the calibration may establish that the right eye wears an ophthalmic lens with a specific identification string, which may be transmitted with each position data or may be transmitted to initiate pairing. Where the right lens may be placed on the left eye, the position data may fall out of the established normal range, for example, where the position data may suggest that the eyes are looking in opposite directions. In such aspects, a notification mechanism may activate to alert the user that he may have placed the lens on the incorrect eye.

Figures 6A, 6B:
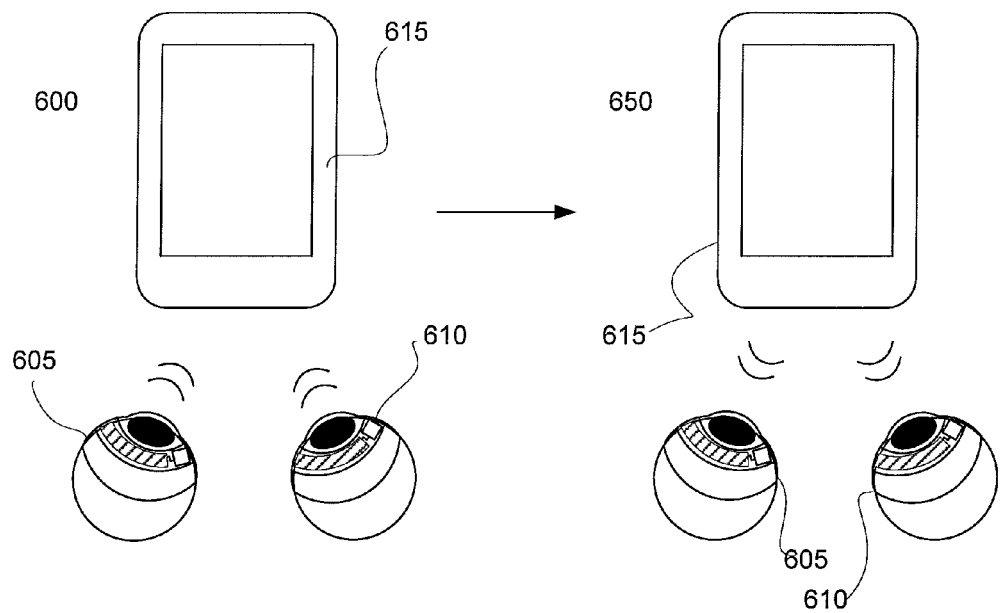
FIGS. 6A-6B illustrate exemplary process steps for wireless communication between two ophthalmic lenses utilizing an external device.

Referring now to FIGS. 6A and 6B, an exemplary embodiment of communication steps between ophthalmic lenses utilizing an external device 615 is illustrated. For illustrative purposes, the external device 615 is illustrated as a handheld device with a screen, for example a smartphone. At step 600, in some exemplary embodiments, FIG. 6A, the left lens 605 and the right lens 610 may transmit positional data to the external device 615. The transmissions may be periodic or almost continuous, depending on the power restrictions between the external device 615 and the ophthalmic lenses 605, 610. For example, where the external device 615 provides the power for the lenses 605, 610, the sample and transmission rate may be higher than where the ophthalmic lenses 605, 610 may comprise their own power source. The left lens 605 and the right lens 610 may transmit the data without a prompt from the external device 615 or from the opposite eye. At step 650, the external device 615 may transmit the positional data to the opposite lens, FIG. 6B. In some exemplary embodiments, the transmission from the external device 615 to the right lens 610 may be synchronized with the transmission to the left lens 605. In other examples, the transmissions to the left lens 605, at step 650, may be responsive to the transmissions from the left lens 605, at step 600.

The external device 615 and the ophthalmic lenses 605, 610 may comprise complementary communication protocols enabling the three devices to wirelessly communicate. In some exemplary embodiments, the communication protocol may comprise a technology that may rely on proximity between the devices, including, for example, infrared, which may limit inadvertent wireless communication with unintended external devices.

Some alternative exemplary embodiments may allow pairing between the ophthalmic lens and the external device through technology typically included in a standard external device, such as, for example, Bluetooth technology. As compared to other wireless communication methods, Bluetooth technology may be relatively common in external devices, and synchronization may not require additional hardware.

Alternatively, the communication protocol may comprise a lower power embodiment, including, for example, ANT or ZigBee technology. This may allow the ophthalmic lens to sample periodically the environment for the external device event data transmission from the external device while also limiting the power loss from the sampling. Low power wireless protocol may generally extend the potential energizable duration of the ophthalmic lens. Complementary wireless protocol profiles may limit the ophthalmic lens to receive transmissions from the intended external device.

In some exemplary embodiments, the pairing may occur prior to use. For example, the ophthalmic lens may be preprogrammed to interact with a specific external device, such as through use of application software that may be downloaded onto the intended external device. In other such embodiments, the ophthalmic lens may include a serial authentication code or electronic pedigree (e-pedigree), which may be unique to a particular ophthalmic lens or an ophthalmic lens pack. The unique code identifying the ophthalmic lens may vary depending on the serialization methods associated with the brand or line of ophthalmic lenses.

The external device may be programmed to recognize a specific serial code. In some exemplary embodiments, the user may program the external device utilizing capture technology to scan or photograph a stock keeping unit (SKU) barcode or quick response (QR) bar code, which may be associated with the authentication serial number. In some such aspects, the SKU or QR barcode may be located on the packaging of the ophthalmic lens, for example, on the individual blister package or on the box for multiple blisters packages, or other common packaging techniques. Initiating the pairing through interaction with the packaging may be preferable over direct interaction with the ophthalmic lens as a means to reduce contamination of or damage to the ophthalmic lens or the eye.

In some exemplary embodiments, the scanned code may specify the identifying attribute of the ophthalmic lens. The identification may allow the external device to communicate specifically with the intended ophthalmic lens. For example, the scanned code may include the authentication code, the Bluetooth profile, infrared wavelength, or infrared signal pattern, depending on the wireless communication technology.

Prior to a communication between the ophthalmic lens and an external device, the two devices may trade or recognize the serial authorization or e-pedigree, for example, through use of a radio frequency identification system. In some exemplary embodiments, an external device event may trigger the external device to transmit an identification or authorization interrogation to the ophthalmic lens. The interrogation may include all, part, or none of the authorization code. For example, the external device may transmit the entire code, and, where the code matches the serial code of the ophthalmic lens, the lens may transmit a response, which may include the serial code or recognition of the correct serial code.

Alternatively, the interrogation may include a portion of the serial code, and the ophthalmic lens may respond with the remaining portion. A successful string may permit further wireless communication. In still further alternatives, the interrogation may not transmit any portion of the serial code but may prompt the ophthalmic lens to transmit the entire code. Where the external device verifies the serial code, wireless communication may continue, and where the serial code does not match, wireless communication may be terminated.

In some exemplary embodiments, the pairing may occur entirely on eye, wherein a user or external device operator may place the external device in proximity to the ophthalmic lens. Utilizing a software application, including, for example, a downloadable mobile application or standard wireless software installed during manufacturing, the user may prompt the external device to scan for the wireless profile or protocol of the ophthalmic lens. Such an initial scan may pair the external device to the ophthalmic lens, for example, through infrared or Bluetooth technology. Future wireless communication may occur where the external device verifies the identity of the ophthalmic lens based on the pairing.

In some exemplary embodiments, the ophthalmic lenses may communicate through a single specified external device. Alternatively, the ophthalmic lenses may be paired with multiple external devices, wherein a proximity to any one of the devices may allow for wireless communication between the two lenses. For example, the external devices may comprise a desktop computer, a television, a tablet, and/or a smartphone. The user may synchronize the ophthalmic lenses with all four external devices, which may allow for communication between lenses when the user may be in proximity to, or more particularly, when the user engages any of the four devices. Utilizing multiple devices may allow for continuous communication without tethering the user to a single device.

As an illustrative example, radio frequency identification (RFID) may be utilized as a means to verify the identity of the ophthalmic lens. Verification through RFID may not require the external device to be in the line of sight of the ophthalmic lens. Such embodiments may limit wireless communication to specific range but not necessarily to a specific location. For example, the external device may be located in a bag or pocket, and wireless communication may still occur where the external device may be within range.

An RFID system may also allow for low power requirements for identification exchange based on the type of tag and reader. In some exemplary embodiments, the ophthalmic lens may include a passive tag, wherein the ophthalmic lens may reply to interrogations from an active reader in the external device. Such an embodiment may conserve power use within the ophthalmic lens. In some such aspects, the interrogation may prompt the ophthalmic lens to begin sampling the defined environment for the external device event data. The ophthalmic lens may be inactive prior to the interrogation, and the sampling may be deactivated after a specified amount of time to conserve energy, for example, when the authentication code may be not verified. Alternatively, the ophthalmic lens may sample at different rates that may vary based on the presence and interfacing demands of an external device.

Figures 7A, 7B, 7C:
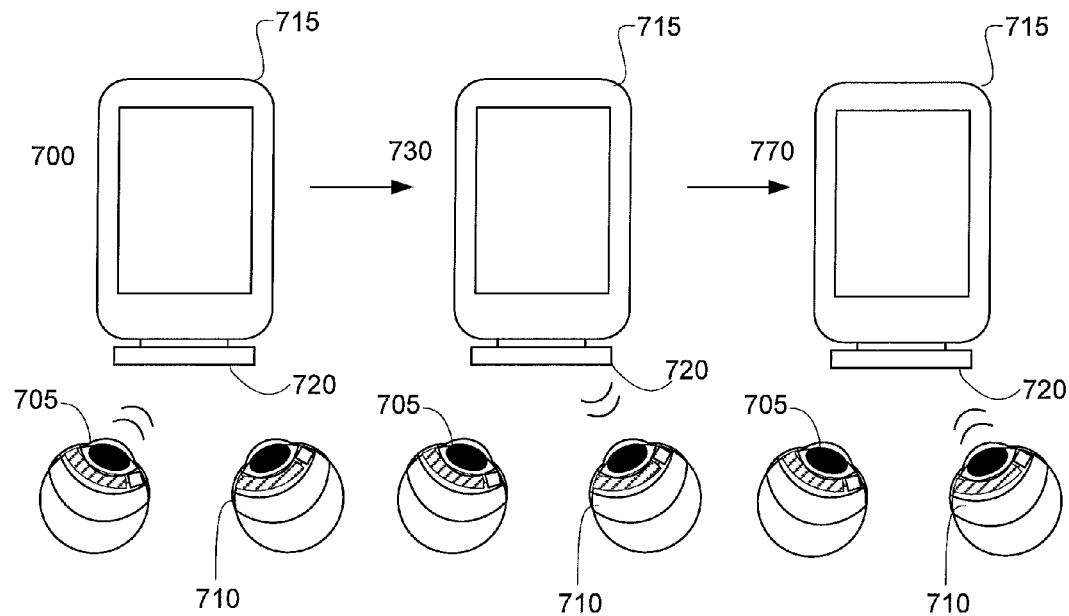
FIGS. 7A-7C illustrate alternative process steps for wireless communication between two ophthalmic lenses utilizing an external device.

Referring now to FIGS. 7A-7C, an alternate exemplary embodiment of communication steps 700, 730, 770 between ophthalmic lenses utilizing an external device 715 is illustrated. For illustrative purposes, as with FIGS. 6A and B, the external device 715 is illustrated as a handheld device with a screen, for example, a smartphone. In some exemplary embodiments, at step 700, the left lens 705 may transmit positional data to the external device 715, and, at step 730, the external device 715 may send that information to the right lens 710. In response in such examples, at step 770, the right lens 710 may reply with positional data.

Alternatively, the right lens 710 may not transmit positional data at 770. In some such embodiments, a unilateral communication may be sufficient to establish relative positions of the two eyes. Though such an embodiment may overcome the line-of-sight issue, a unilateral communication may require one lens to comprise more processing and power capabilities than the opposite eye. Accordingly, such aspects may reduce the alleviating benefits of utilizing an external device.

In some exemplary embodiments, particularly where only one lens may comprise the energizable functionality component, unilateral communication may be more practical and efficient. For example, an energizable ophthalmic lens may comprise a dispensing mechanism, wherein the lens may dispense an active agent, for example, based on a biomarker concentration within the tear fluid. The ophthalmic lenses may exchange or one lens may unilaterally send biomarker level data to the opposite lens. Utilizing data from both eyes may allow for a more accurate assessment of the biomarker levels and the active agent needs of the user.

In some alternative embodiments, a transmission adapter or dongle 720 may be attached to an external device 715, wherein the dongle 720 may allow the external device 715 to wirelessly transmit and receive data to and from the right lens 710 and the left lens 705. This implementation may be preferred, for example, where the wireless protocol necessary to communicate with the ophthalmic lenses 705, 710 may be not implemented in the external device 715. For example, the design constraints on the ophthalmic device 705, 710 may require the use of a custom low-power communication protocol.

As an illustrative example, the transmission adapter 720 may allow the external device 715 to transmit and receive data through an infrared transmission to and from the ophthalmic lenses 705, 710. Prior to use, the transmission adapter 720 may be paired with the specific ophthalmic lenses 705, 710, for example, where the transmission adapter 720 may be calibrated to specific infrared wavelengths or pulse patterns. As may be common in digital communication, device addressing, error correction, and encryption may be included in the communication protocol.

In some exemplary embodiments, the transmission adapter 720 may comprise a wireless protocol specifically designed to allow for asymmetric communication and data exchange between an ophthalmic lens and an external device. Such asymmetrical communication may shift the processing and power burden from the ophthalmic lens to the external device, which may not be as limited in size.

Figure 8A:
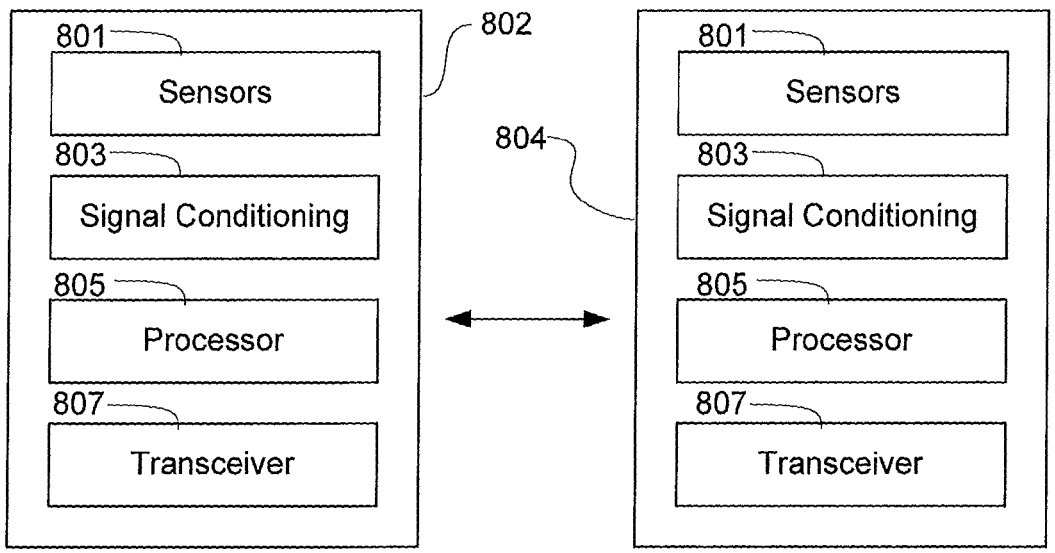
FIG. 8A illustrates a system in which an external device is not present.
Figure 8B:
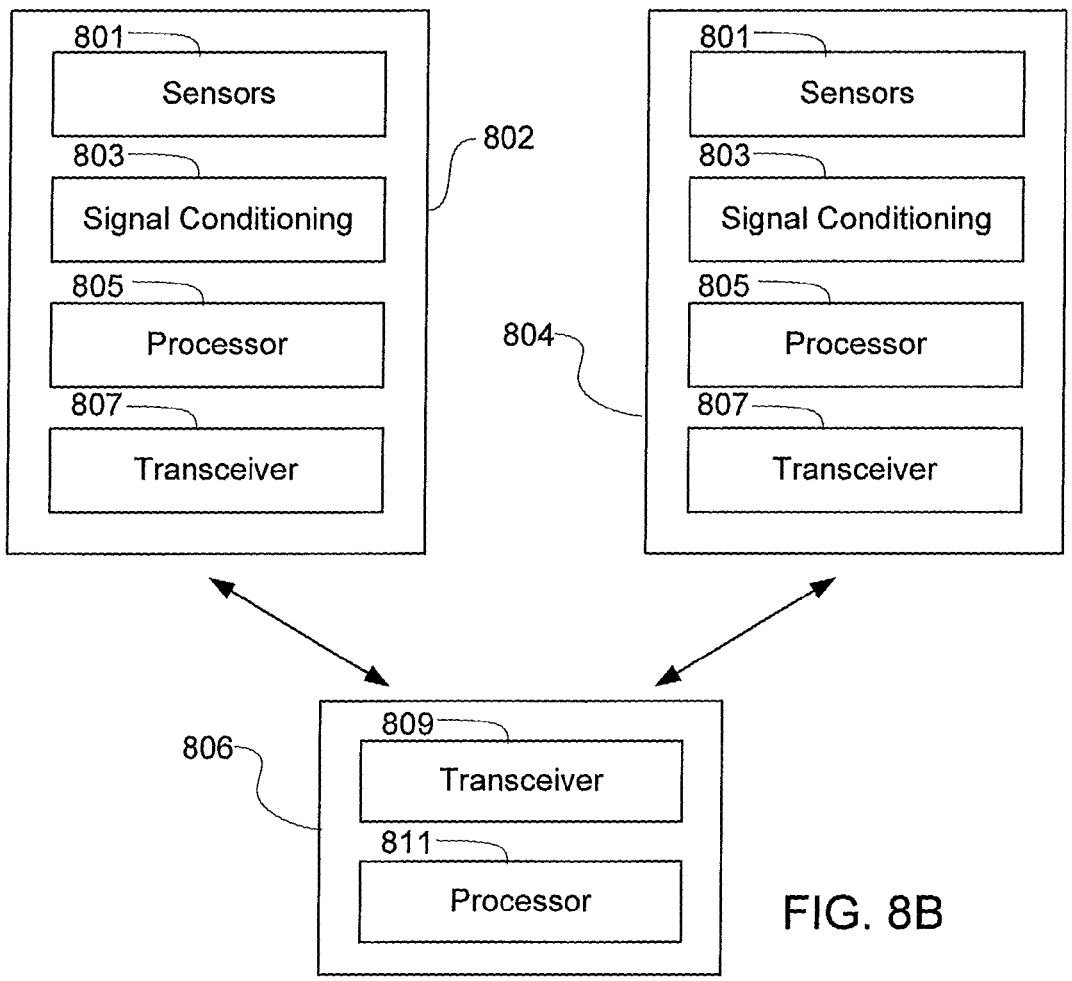
FIG. 8B illustrates a system in which an external device offloads, assists, or augments some processing and/or communication functions of the ophthalmic devices.

FIG. 8A illustrates a system in which an external device may not be present, whereas FIG. 8B illustrates a system in which an external device may assist two ophthalmic devices in communication and/or processing. Ophthalmic devices 802 and 804 may represent, for example, contact lenses on a user's right and left eyes. Each contact lens may contain sensors 801, for example to determine and/or acquire one or more of ambient light level, lid position, muscle activity, gaze direction, and images. Signal conditioning circuitry 803 may be employed to interface the sensors 801 to processors 805, for example with amplifier and analog-to-digital converters. Processors 805 in each lens 802, 804 may consider sensor inputs and then activate output functions according to programming, for example, changing the focus of a variable optic when a blink pattern may be detected. The lenses may also comprise transceivers 807 to enable communication with each other or with an external device. The communication channel may include, but may be not limited to, light, sound, ultrasonic, and radio frequency.

In FIG. 8B, an external device 806 may communicate with each lens in contrast to both lenses 802, 804 only communicating with each other. In some exemplary embodiments, the lenses 802, 804 may continue to communicate with each other in addition to communicating with the external device 806. The external device 806 may facilitate communication between the two ophthalmic devices 802, 804 and may ease the processing and communication burdens on the ophthalmic devices 802, 804.

The application requirements of the ophthalmic device may be quite demanding relative to the available area, volume, and battery capacity. For example, processing an acquired signal to determine muscle activity or processing an image for storage may require the computational power typically associated with a central processing unit, co-processor, digital signal processor, field-programmable gate array (FPGA), or microcontroller. Die size and/or current consumption may preclude integration of such processors into an ophthalmic device. Where such functions may be offloaded to an external device, the processor in the ophthalmic device may be much simpler, for example a small, low-power, custom logic block implementing a state machine.

The communication demands on an ophthalmic device may also be very demanding relative to the available size and current. Without an external device, the current consumption in an ophthalmic device's transmitter and/or receiver may be prohibitively large. An external device 806 may comprise a higher-power transmitter and receiver 809 as well as a processor 811. In some exemplary embodiments, the average current consumption to communicate between two ophthalmic devices 802, 804 may be reduced from milliamps to micro amps where milliamps of current may be used in an external device's transceiver 809. In some such exemplary embodiments, the ophthalmic device transceiver complexity and current consumption may be reduced, for example, through reduced transmitter output power, receiver gain, and coding overhead. Likewise, the complexity may be more easily absorbed into the external device, which may have fewer constraints on size and current than an ophthalmic lens.

Figure 9:
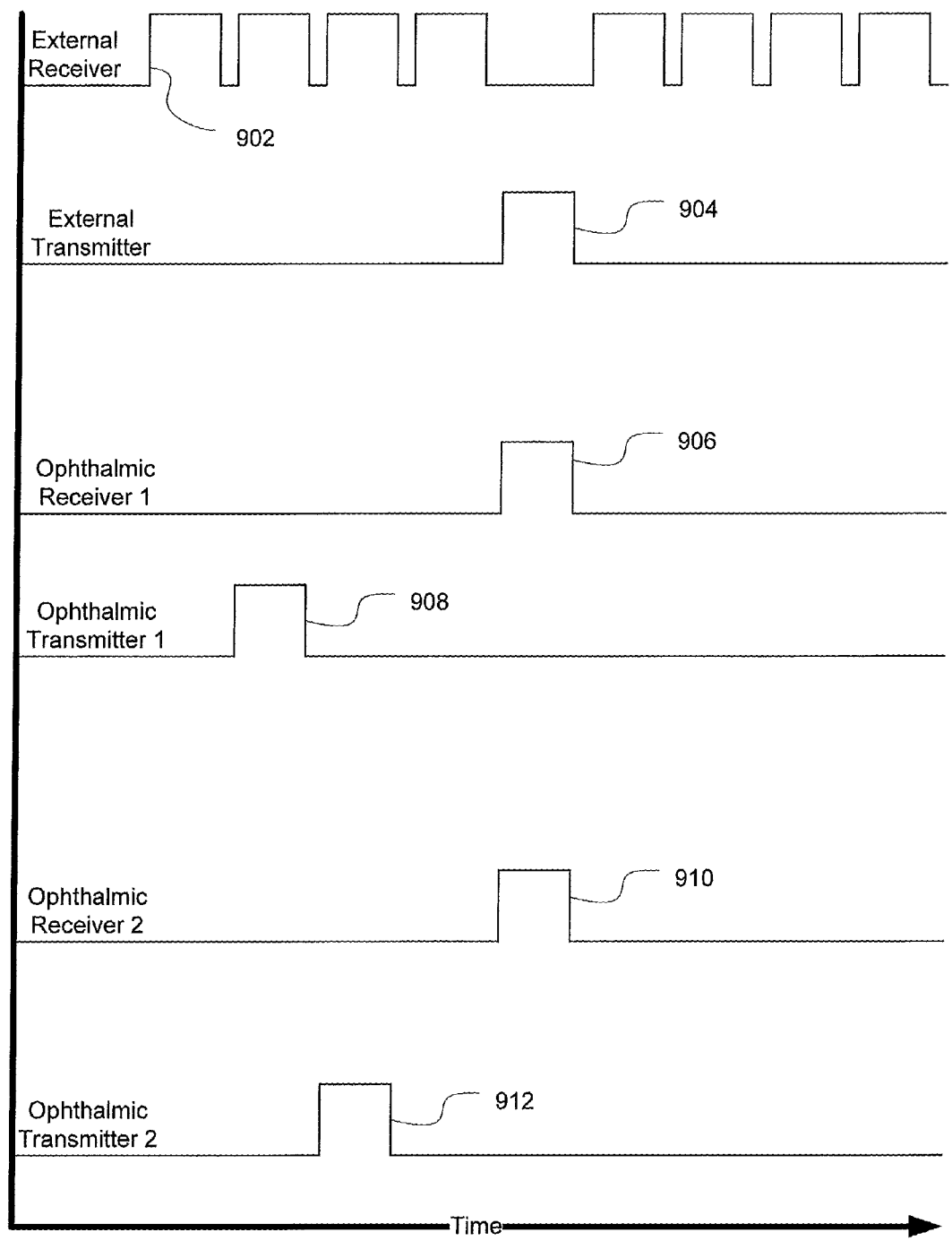
FIG. 9 illustrates exemplary timing of transmitters and receivers in an ophthalmic system including an external device.

Referring now to FIG. 9, there is illustrated an exemplary embodiment of transmission and reception timing for a system including two ophthalmic devices and one external device. In this exemplary illustration, a transmitter or receiver in the "on" state is indicated by a "high" state or pulse, and activity is plotted versus time. At 902, the external device's receiver may periodically turn on to listen for communication from the ophthalmic devices.

During the first pulse, no communication may occur from the ophthalmic devices; accordingly, the ophthalmic transmitters 908 and 912 may be low during this period. In the second period of the external receiver 902, the ophthalmic transmitter 1 may transmit an output at 908. For example, this communication may be from the right contact lens sending three-dimensional coordinates from an accelerometer sensor to indicate gaze direction.

During the third external receiver period, the ophthalmic transmitter 2 may transmit an output at 912. In some exemplary embodiments, the output at 912 may be the left contact lens sending three-dimensional coordinates, similarly to the right lens at 908.

During the fourth external receiver period, no transmissions may take place from the ophthalmic devices, but the external device may be processing the results from the two recent transmissions. The external device may, for example, compute the gaze direction of each lens in three-dimensional space in front of the user and determine the point at which the gaze of each eye converges. Further, the external device may determine that detected convergence of gaze may be associated with the desire to read, which may prompt an activation of variable-focus lenses in the ophthalmic devices.

At 904, the external transmitter may output a signal during an off period of the external receiver 902. The signal may comprise a command to activate lens drivers in the ophthalmic devices. Also at this time, both ophthalmic receivers are listening at 906 and 901. Following receipt of the command, the ophthalmic devices may active their lenses. In some exemplary embodiments, the communication may continue (not illustrated) to process additional sensor inputs, synchronize time bases, and/or transmit/receive data.

Materials for Insert-Based Ophthalmic Lenses

In some exemplary embodiments, a lens type may be a lens that includes a silicone-containing component. A "silicone-containing component" may be one that contains at least one [—Si—O—] unit in a monomer, macromer, or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

In some exemplary embodiments, the ophthalmic lens skirt, which sometimes may be called an insert encapsulating layer, that surrounds the insert may comprise standard hydrogel lens formulations. Exemplary materials with characteristics that may provide an acceptable match to numerous insert materials may include the Narafilcon family; including Narafilcon A and Narafilcon B. Alternatively, the Etafilcon family; including Etafilcon A may represent good exemplary material choices. A more technically inclusive discussion follows on the nature of materials consistent with the art herein; but it may be clear that any materials that may form an acceptable enclosure or partial enclosure of the sealed and encapsulated inserts are consistent and included.

Suitable silicone containing components include compounds of Formula I

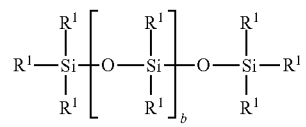

where:

$R^1$ may be independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it may be understood that when b may be other than 0, b may be a distribution having a mode equal to a stated value;

wherein at least one $R^1$ comprises a monovalent reactive group, and in some embodiments between one and three $R^1$ comprise monovalent reactive groups.

As used herein "monovalent reactive groups" are groups that may undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl (meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof, and the like.

In some exemplary embodiments, b may be zero, one $R^1$ may be a monovalent reactive group, and at least three $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-, 2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyltris(trimethylsiloxy) silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another exemplary embodiment, b may be 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b may be 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another exemplary embodiment, b may be 5 to 400 or from 10 to 300, both terminal $R^1$ comprise monovalent reactive groups and the remaining $R^1$ are independently selected from monovalent alkyl groups having 1 to 18 carbon atoms that may have ether linkages between carbon atoms and may further comprise halogen.

In one exemplary embodiment, where a silicone hydrogel lens may be desired, the lens of the present invention will be made from a reactive mixture comprising at least about 20 and preferably between about 20 and 70% wt silicone containing components based on total weight of reactive monomer components from which the polymer may be made.

In another exemplary embodiment, one to four $R^1$ comprises a vinyl carbonate or carbamate of the formula:

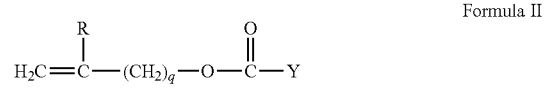

Formula II wherein: Y denotes O—, S— or NH—;
R denotes hydrogen or methyl; d may be 1, 2, 3 or 4; and q may be 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris (trimethylsiloxy)silane]; 3-[tris (trimethylsiloxy)silyl]propyl allyl carbamate; 3-[tris (trimethylsiloxy)silyl]propyl vinyl carbamate; trimethylsilylethyl vinyl carbonate; trimethylsilylmethyl vinyl carbonate, and

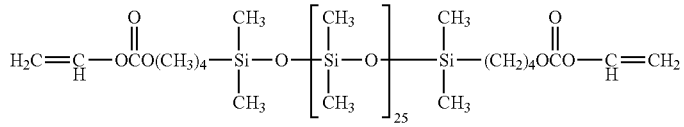

Where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

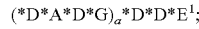

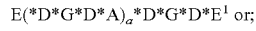

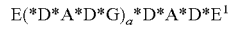  Formulae IV-VI wherein:
D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

$a$ may be at least 1;

A denotes a divalent polymeric radical of formula:

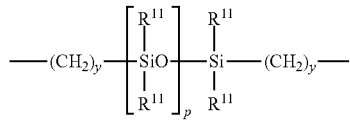

Formula VII $R^{11}$ independently denotes an alkyl or fluoro-substituted alkyl group having 1 to 10 carbon atoms that may contain ether linkages between carbon atoms; y may be at least 1; and p provides a moiety weight of 400 to 10,000; each of E and $E^1$ independently denotes a polymerizable unsaturated organic radical represented by formula:

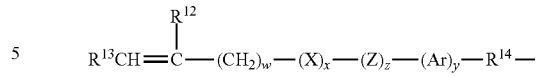

Formula VIII wherein: $R^{12}$ may be hydrogen or methyl; $R^{13}$ may be hydrogen, an alkyl radical having 1 to 6 carbon atoms, or a —CO—Y—$R^{15}$ radical wherein Y may be —O—, Y—S— or —NH—; $R^{14}$ may be a divalent radical having 1 to 12 carbon atoms; X denotes —CO— or —OCO—; Z denotes —O— or —NH—; Ar denotes an aromatic radical having 6 to 30 carbon atoms; w may be 0 to 6; x may be 0 or 1; y may be 0 or 1; and z may be 0 or 1.

A preferred silicone-containing component may be a polyurethane macromer represented by the following formula:

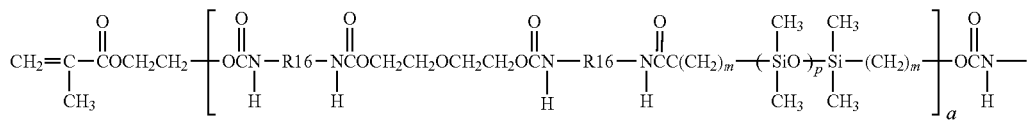

Formula IX

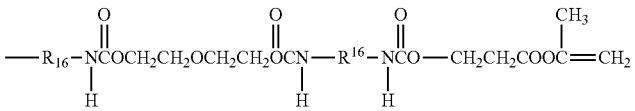

wherein $R^{16}$ may be a diradical of a diisocyanate after removal of the isocyanate group, such as the diradical of isophorone diisocyanate. Another suitable silicone containing macromer may be compound of formula X (in which x+y may be a number in the range of 10 to 30) formed by the reaction of fluoroether, hydroxy-terminated polydimethylsiloxane, isophorone diisocyanate and isocyanatoethylmethacrylate.

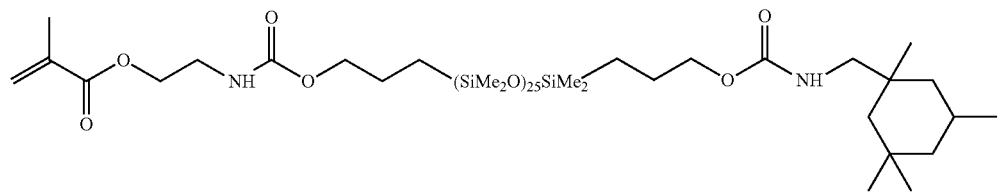

Formula X

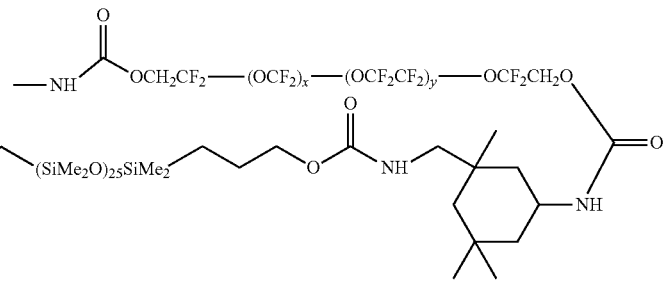

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkanges and crosslinkable monomers containing polyether and polysiloxanyl groups. Any of the foregoing polysiloxanes may also be used as the silicone-containing component in the present invention.

Although shown and described in what is believed to be the most practical and preferred embodiments, it may be apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens system capable of wireless communication through utilization of an external device, the ophthalmic lens system comprising:
    a first ophthalmic lens wearable on a first eye for wirelessly communicating with the external device, wherein the first ophthalmic lens comprises:
        a first lens transmitter,
        a first lens receiver,
        a first lens processor in electrical communication with the first lens transmitter and the first lens receiver,
        and a first soft lens portion for placement on the first eye and encapsulation of at least a portion of one or more the first lens transmitter, the first lens receiver, and the first lens processor, and wherein the external device comprises a device power source, a device transmitter, a device receiver, and a device processor in electrical communication with the device power source, the device transmitter, and the device receiver; and
    a second ophthalmic lens wearable on a second eye wirelessly communicating with one or both the first ophthalmic lens and the external device, wherein the second ophthalmic lens comprises:
        a second lens transmitter,
        a second lens receiver,
        a second lens processor in electrical communication with the second lens transmitter and the second lens receiver,
        and a second soft lens portion for placement on the second eye and encapsulation of at least a portion of one or more the second lens transmitter, the second lens receiver, and the second lens processor, and wherein the device processor is configured for more computational power than one or both the first lens processor and the second lens processor,
        wherein the first ophthalmic lens, the second ophthalmic lens and the external device communicate with each other such that the first and second ophthalmic lenses perform one or more coordinated functions.

2. The ophthalmic lens system of claim 1, wherein one or both the first ophthalmic lens and the second ophthalmic lens further comprises a lens power source to energize the ophthalmic lens system, wherein the lens power source comprises less energization capabilities than the external device power source.

3. The ophthalmic lens system of claim 1, wherein the external device receiver has a higher sensitivity than the first and second lens receivers.

4. The ophthalmic lens system of claim 1, wherein the external device is capable of energizing the ophthalmic lens system.

5. The ophthalmic lens system of claim 1 further comprising a first functionality, wherein the first functionality comprises a primary purpose of the ophthalmic lens system.

6. The ophthalmic lens system of claim 1, wherein one or both the first lens receiver and the first lens transmitter are capable of communicating with one or both the second lens receiver and the second lens transmitter.

7. The ophthalmic lens of claim 1, wherein one or both the first lens processor and the second lens processor comprises a logic block.

8. The ophthalmic lens system of claim 1, wherein the first ophthalmic lens further comprises a first position detection mechanism to track one or both a gaze position of the first eye or a lid position of a first eyelid.

9. The ophthalmic lens system of claim 1, wherein the wireless communication comprises an exchange of first data between the first ophthalmic lens and the external device and an exchange of second data between the external device and the second ophthalmic lens.

10. The ophthalmic lens system of claim 1, wherein the wireless communication comprises a wireless protocol that requires less energy and computational power from the ophthalmic lens system than the external device.

11. The ophthalmic lens system of claim 3, wherein the device receiver comprises a low-noise amplifier.

12. The ophthalmic lens system of claim 5, wherein one or both the ophthalmic lens system and the external device provide programming or operating the functionality of the ophthalmic lens system.

13. The ophthalmic lens system of claim 8, wherein the second ophthalmic lens further comprises a second position detection mechanism to track one or both a gaze position of the second eye or a lid position of a second eyelid.

14. The ophthalmic lens system of claim 9, wherein the exchange of second data comprises a transmission of data from the external device to the second ophthalmic lens, wherein the transmission is responsive to the exchange of first data.

15. The ophthalmic lens system of claim 10, wherein the external device comprises a wireless communication mechanism for the wireless protocol.

16. The ophthalmic lens system of claim 12, wherein the first functionality comprises an operation of the first ophthalmic lens.

17. The ophthalmic lens system of claim 12, wherein the first functionality comprises an operation of the first ophthalmic lens and the second ophthalmic lens in conjunction.

18. The ophthalmic lens system of claim 13 further comprising a signal conditioning mechanism to allow interfacing between the first position detection mechanism and one or both the first lens processor and the device processor and between the second position detection mechanism and one or both the second lens processor and the device processor.

19. The ophthalmic lens system of claim 13, wherein the ophthalmic lens system is configured for tracking convergence between the first eye and the second eye, wherein the convergence is based on one or both the gaze position and the lid position of the first eye and the second eye.

20. The ophthalmic lens system of claim 13, wherein one or more of the external device, the first ophthalmic lens, and the second ophthalmic lens discern between voluntary movements and involuntary movements of one or more of the gaze position of the first eye, the gaze position of the second eye, the lid position of the first eye, and the lid position of the second eye.

21. The ophthalmic lens system of claim 15, wherein the wireless communication mechanism comprises a dongle, wherein the dongle attaches to the external device.

22. The ophthalmic lens system of claim 18, wherein the signal conditioning mechanism comprises an amplifier.

23. The ophthalmic lens system of claim 18, wherein the signal conditioning mechanism comprises an analog-to-digital converter.

\* \* \* \* \*